(12) United States Patent
Bauer-Reich et al.

(10) Patent No.: US 9,964,532 B2
(45) Date of Patent: May 8, 2018

(54) BIODEGRADABLE SOIL SENSOR, SYSTEM AND METHOD

(71) Applicant: NDSU RESEARCH FOUNDATION, Fargo, ND (US)

(72) Inventors: Cherish Bauer-Reich, Fargo, ND (US); Justin Hoey, Fargo, ND (US); Robert Sailer, Fargo, ND (US); Nathan Schneck, Fargo, ND (US); Chad Ulven, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 35 days.

(21) Appl. No.: 14/760,867

(22) PCT Filed: Jan. 15, 2014

(86) PCT No.: PCT/US2014/011662
§ 371 (c)(1),
(2) Date: Jul. 14, 2015

(87) PCT Pub. No.: WO2014/113460
PCT Pub. Date: Jul. 24, 2014

(65) Prior Publication Data
US 2017/0045487 A1 Feb. 16, 2017

Related U.S. Application Data

(60) Provisional application No. 61/752,971, filed on Jan. 15, 2013.

(51) Int. Cl.
*G01N 33/24* (2006.01)
*G01N 27/02* (2006.01)
(Continued)

(52) U.S. Cl.
CPC ............. *G01N 33/24* (2013.01); *G01N 27/02* (2013.01); *H01Q 1/2258* (2013.01); *H01Q 1/38* (2013.01);
(Continued)

(58) Field of Classification Search
CPC ....... G01N 33/24; G01N 27/02; H01Q 1/2258
See application file for complete search history.

(56) References Cited

U.S. PATENT DOCUMENTS 5,236,570 A   8/1993  Ma et al.
8,001,990 B2  8/2011  Schmidt
(Continued)

FOREIGN PATENT DOCUMENTS

CN   1547887 A   11/2004
CN   201527407 U   7/2010
(Continued)

OTHER PUBLICATIONS

Bhattacharya, S., et al. "Micro Cold Spray Direct Write Process" Houston: ASME 2012, International Mechanical Engineering Congress and Exposition, Nov. 9-15, 2012, vol. 7, ISBN: 978-0-7918-4523-3, p. 907-911; Retrieved from the Internet: URL:http://proceedings.asmedigitalcollection.asme.org/proceeding.aspx?articleid=1751556.
(Continued)

*Primary Examiner* — Jermele M Hollington
*Assistant Examiner* — Feba Pothen
(74) *Attorney, Agent, or Firm* — McKee, Voorhees & Sease, PLC

(57) ABSTRACT

A biodegradable soil sensor, a biodegradable soil sensing system and method for obtaining soil information is provided. The biodegradable sensor may include one or more electrically conductive bioinert traces and a biodegradable substrate having a printed circuit of the one or more elec-
(Continued)

(a)

(b)

trically conductive bioinert traces. A biodegradable antenna may be formed by at least one of the one or more electrically conductive bioinert traces. A sensor may be connected to the one or more electrically conductive bioinert traces. The sensor may also include a biodegradable encapsulation layer housing the biodegradable substrate and the electrically conductive bioinert traces.

21 Claims, 8 Drawing Sheets

(51) Int. Cl.
*H01Q 1/22* (2006.01)
*H01Q 1/38* (2006.01)
*H04B 7/185* (2006.01)
*G01N 33/00* (2006.01)

(52) U.S. Cl.
CPC ....... *H04B 7/1851* (2013.01); *G01N 33/0075* (2013.01); *G01N 2033/245* (2013.01)

(56) References Cited

U.S. PATENT DOCUMENTS

| | | | |
|---|---|---|---|
| 8,063,774 B2 | 11/2011 | Anderson | |
| 8,089,287 B2* | 1/2012 | Izadnegahdar | G01N 27/223 324/663 |
| 2008/0140185 A1* | 6/2008 | Kiser | C08G 18/10 623/1.42 |
| 2008/0168710 A1* | 7/2008 | MacKenzie | A01G 9/02 47/65.9 |
| 2009/0018235 A1* | 1/2009 | Nascimento | C08L 67/04 523/128 |
| 2009/0112475 A1* | 4/2009 | Christy | A01B 79/005 702/5 |
| 2009/0303071 A1* | 12/2009 | Anderson | G01D 11/245 340/693.5 |
| 2012/0223293 A1* | 9/2012 | Borenstein | B82Y 10/00 257/40 |

FOREIGN PATENT DOCUMENTS

| | | |
|---|---|---|
| WO | 2011069563 A1 | 6/2011 |
| WO | 2012041521 A1 | 4/2012 |

OTHER PUBLICATIONS

Kumar, R., et al. "Biodegradation of Flax Fiber Reinforced Poly Lactic Acid", eXPRESS Polym Lett. Jul. 2010, vol. 4, No. 7, pp. 423-430.

NDSU Research Foundation, PCT/US14/11662, filed Jan. 15, 2014, "Notification of Transmittal of International Preliminary Report on Patentability", dated Feb. 26, 2015, 18 pages.

NDSU Research Foundation, PCT/US14/11662, filed Jan. 15, 2014, "The International Search Report and the Written Opinion of the International Searching Authority, or the Declaration" dated Apr. 28, 2014, 14 pages.

* cited by examiner

BIODEGRADABLE SOIL SENSOR, SYSTEM AND METHOD

CROSS-REFERENCE TO RELATED APPLICATIONS

This is a National Phase application claiming priority to PCT/US2014/01162 filed Jan. 15, 2014 which claims priority under 35 U.S.C. § 119 to provisional application U.S. Ser. No. 61/752,971 filed Jan. 15, 2013, all of which are herein incorporated by reference in their entireties.

BACKGROUND OF THE INVENTION

I. Field of the Invention

The present disclosure relates to a biodegradable soil sensor, system and method. More specifically, but not exclusively, the present disclosure relates to a biodegradable soil sensor, a biodegradable soil sensing system and method for obtaining soil information.

II. Description of the Prior Art

Current methods of assessing crop health rely on monitoring spectral content of light reflected by the plants. These methods use passive sensors on satellites and aircraft or active sensors mounted on tractors. There are drawbacks to these methods in that many variables can impact reflectivity including nutrient deficiencies, differences among varieties, field resolution, disease, etc. In particular, soil type is one of the more significant variables in using this method of nutrient sensing. While these tools are useful in examining crop health, they are indirect measurements and ultimately require previous knowledge of the soil conditions and specialized algorithms to properly evaluate crop conditions.

Therefore, it is an object, feature, or advantage of the present disclosure to provide a biodegradable sensor for measuring crop health by taking direct measurements from the soil.

While there are commercially available products that directly measure moisture and temperature of the soil, these sensors are typically large, bulky, and expensive. This means that fewer sensors are available within a particular planting area generating low resolution data which may not give accurate information about conditions throughout a particular field.

Therefore, another object, feature, or advantage of the present disclosure is to provide a biodegradable soil sensing system that is sufficiently economical so as to be capable of being deployed in number commensurate with the number of seed planted for generating a high resolution map of soil conditions.

Another object, feature, or advantage of the present disclosure is to provide a biodegradable sensor that is small, inexpensive, robust, easy to deploy, and easy to read.

Increasing the number of sensors or sensor nodes in a field to increase the resolution of the data mapping field conditions is often limited by the cost of the sensor, deployment, retrieval, operation, etc. Over time deployed sensors interact with the soil and ground moisture, and degradation of the sensor is inevitable, but retrieval/removal of large numbers of sensors is also a problem. Moreover, sensor degradation could contaminate the soil and/or negatively impact the quality or safety of crops and the soil.

Therefore, another object, feature, or advantage of the present disclosure is to provide a method using biodegradable sensors that can be deployed, for example, using a seeder or planter, and where the sensor is generally bioinert, non-bioaccumulating or otherwise biodegradable and not retrieved.

A still further object, feature, or advantage of the present disclosure is to provide a biodegradable sensor that is passive thereby eliminating the need for an internal battery.

Yet another object, feature, or advantage of the present disclosure is to provide a sensor that can be monitored using vehicles, tractors, planes, or other equipment passing through or above the field.

One or more of these and/or other objects, features or advantages of the present disclosure will become apparent from the specification and claims that follow.

SUMMARY OF THE INVENTION

The present disclosure provides a biodegradable soil sensor, a biodegradable soil sensing system and method for obtaining soil information.

One exemplary embodiment provides a biodegradable soil sensor. The biodegradable sensor may include one or more electrically conductive bioinert traces and a biodegradable substrate having a printed circuit of the one or more electrically conductive bioinert traces. A biodegradable antenna may be formed by at least one of the one or more electrically conductive bioinert traces. A sensor may be connected to the one or more electrically conductive bioinert traces. The sensor may also include a biodegradable encapsulation layer housing the biodegradable substrate and the electrically conductive bioinert traces.

Another embodiment provides a method for obtaining soil information using a biodegradable encapsulated sensor having one or more electrically conductive bioinert traces carried by a biodegradable substrate. The biodegradable encapsulated sensor may be deposited underground, for example, using a seeder, planter or other like implement. Soil-related parameters may be sensed with at least one of the one or more electrically conductive bioinert traces. The soil-related parameters may be collected with a reading device. In a preferred form, the biodegradable sensor is left in the soil to biodegrade.

Yet another embodiment provides a soil sensing system. The system may be configured using a biodegradable soil sensor having one or more biodegradable and bioinert components. The components may be include, for example, a substrate, a plurality of printed electrical traces and a circuit formed with one or more of the plurality of printed electrical traces. A sensing element may be connected to the circuit with one or more of the plurality of printed electrical traces and an antenna may be formed from at least one or more of the plurality of printed electrical traces. Soil-related parameters may be collected from one or more of the biodegradable soil sensors using a reader.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE PREFERRED EMBODIMENTS

A large emphasis is been placed on precision agriculture as a method of improving plant health to maximize crop yields, reduce the impact of new farming practices on the environment (i.e. over fertilization), and to improve profits in rural communities. One of the primary methods of assessing crop health relies on monitoring spectral content of light reflected by the plants. These methods use passive sensors on satellites and aircraft or active sensors mounted on tractors. There are drawbacks to these methods in that many variables can impact reflectivity including nutrient deficiencies, differences among varieties, field resolution, disease, etc. In particular, soil type is one of the most significant variables in using this method of nutrient sensing. While these tools are useful in examining crop health, they are indirect measurements and ultimately require previous knowledge of the soil conditions and specialized algorithms to properly evaluate crop conditions.

Figure 1:
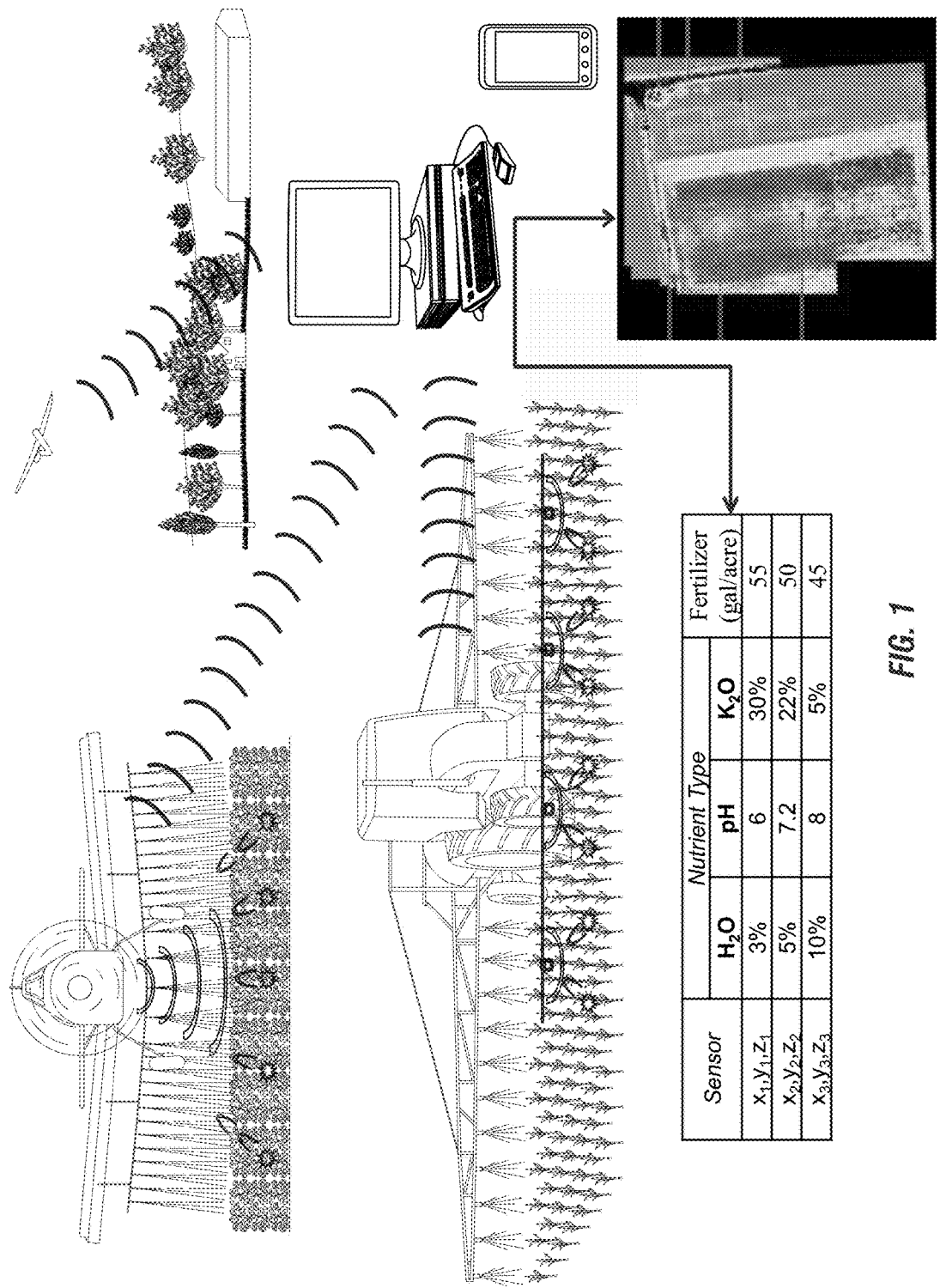
FIG. 1 is a pictorial representation of a method for collecting sensor data in accordance with an illustrative embodiment.

While there are commercially available products that directly measure moisture and temperature of the soil, these products are typically large, bulky, and expensive. This means that fewer sensors are available within a particular planting area generating low resolution data which may not give accurate information about conditions throughout a particular field. Higher resolution options include hand-held devices, but these have many drawbacks, including not allowing for adaptive application of fertilizers. To more accurately assess soil conditions in an effort to maintain plant health and improve precision farming methods, a new type of sensor is needed. The sensor should be very small, inexpensive, robust, easy to place, and easy to read. Ideally, the sensor will give in-situ measurements that provide information, for example, in real time about soil conditions in plots as small as a square meter. A sensor that is sufficiently small could easily be introduced through a seeder or planter or like implement during crop planting and could use passive Radio Frequency Identification (RFID) communications protocols to power the sensor and communicate with a reader mounted on a tractor or all-terrain vehicle, aircraft or other means for reading the sensors as shown by way of illustration in FIG. 1. Using the passive communication methods of the present disclosure eliminate the need for batteries, making it easier to create a small sensor void of toxic materials.

Degradation of the soil sensor is inevitable due to its interaction with the soil. After sensors fail, removal is necessary to mitigate any leaching of toxic materials. Removal of large numbers of these small sensors, however, is problematic due to the time and cost of doing so. Therefore, the sensor of the present disclosure is disposable, biodegradable/bioinert, and non-toxic, which allows the sensor to be left in the soil without any adverse effects to the soil or crops. Moreover, standard electrical circuitry contains tin, silver and/or copper solder and interconnects. These heavy metals may unwantedly leach into the soil. Accordingly, aspects of the present disclosure include direct-write printing of electrical circuitry that eliminates the use of heavy metals in place of more soil-friendly metals, such as aluminum and magnesium.

To address the current drawbacks in the art, a biodegradable soil sensor, a biodegradable soil sensing system and method for obtaining soil information is provided.

According to one aspect, the sensor is configured to be disposable, biodegradable, and non-toxic. The present disclosure uses the term "biodegradable" to describe one or more features, benefits or aspects of the invention. The term "biodegradable" could be used interchangeably with the terms bioinert, and/or non-bioaccumulating for description purposes herein. These and/or other features of the sensor allow it to be placed in soil and left in place even after it is no longer functional without contaminating the soil or negatively impacting the quality or safety of crops grown in such soil. For example, standard tin/lead solders used for much electronics manufacturing are eliminated through the implementation of a biodegradable sensor as set forth herein. According to another aspect, the sensor could be configured to improve ground soil quality by releasing locked-in nutrients as it degrades over time.

The present disclosure provides a sensor to directly monitor the soil environment by being deployed (e.g., planted) in the soil. The sensor, in its final form, could be configured to the size of a soybean, corn kernel, or like-size seed. The sensor is preferably configured from renewable, environmentally-safe materials. Applications of the present disclosure enable improvements to crop health and higher yields as a result of the higher resolution of data acquired from any one given field. Aspects of the invention can reduce cost by improving the accuracy of precision farming, making adaptive application of fertilizer more accurate. Moreover, applications of the present disclosure can aid in early detection of problematic soil conditions, improving chances that remediation will be effective.

Overview

The present disclosure includes, amongst others, some keys areas of focus. These areas, include for example, the use of direct-write processes, processing of natural-fiber reinforced composites (i.e., biocomposites) as components or subsystems (e.g., substrate, sensor, and antenna). All of these areas are integral to developing a sensor, method and system, though some areas may play a more advanced role than others for the different areas of development.

Substrate Approach

One aspect of the present disclosure includes the use of a substrate for carrying circuit board. In a preferred form, the substrate is biodegradable and can be left in the soil to degrade and does not have to be retrieved from the soil at any time. Also, the circuit board is preferably a printed circuit board (PCB).

A suitable substrate which can support the circuitry needed to remain operable for a required time and then degrade into the soil, can utilize various polymers derived from renewable resources in combination with natural fibers as reinforcement to create a biodegradable biocomposite substrate. The biocomposites can be designed to meet critical functional specifications for the PCB such as flexibility, conductivity, density, surface roughness, degradation, etc.

Natural fibers of interest for such applications include bast fibers such as flax, hemp, jute, and kenaf. These fibers, mainly composed of cellulose, can provide additional strength, stiffness, and toughness to brittle polymers when introduced in accordance with desired aspects of the present invention. In addition, through co-polymerization of different renewable-based biodegradable polymers, the rate of biodegradation can also be controlled, much like controlled delivery of medication in pharmaceuticals. In this manner, a PCB substrate can be configured which can be designed to biodegrade at a controlled rate when embedded in soil.

Biodegradable polymers made from a variety of renewable feedstocks such as vegetable oils, starches, celluloses, proteins, and lignin are suitable for use in different engineering applications. Example polymers considered herein include, for example, polylactic acid (PLA), polyglycolic acid (PGA), polybeta-hydroxy butyrate (PHB), and polybeta-hydroxy butyrate-covalerate (PHBV). Biodegradable polymers, such as PLA, are readily available from various sources and are derived from renewable resources.

According to one aspect of the invention, biodegradable composite substrates composed of a polylactic acid (PLA) thermoplastic (derived from corn starch) matrix and flax fiber reinforcement are developed. The PLA/flax fiber biocomposites may be fabricated, for example, using compression molding. Alternating layers of PLA film and flax fiber fabric, the materials may be stacked in a pre-heated (e.g., 100 mm×200 mm) mold and then heated under pressure to melt the film and impregnate the flax fiber. Sufficient time may than be allowed for the PLA resin to wet the flax fiber. The sample may then be cooled to room temperature and the composite removed from the mold.

According to another aspect of the present disclosure, bast natural fibers such as flax may be used to reinforce biobased polymers such as PLA in a composite as a means to strategically control stiffness and degradation rates in substrates for printed circuitry.

Once the biocomposite substrate is configured with a set of desired properties (e.g., physical and mechanical) for the PCB of the sensor, sheet extrusion or compression molding of thin plates may be used to produce coupons for testing. A detailed study on the rate of biodegradation may be conducted with varying levels of temperature, humidity, and number and type of microbes present (using, e.g., ASTM Method D5988) to simulate a wide range of potential soil conditions the sensors may be placed, deployed and/or planted. If the degradation rate is too quick or too slow, the biocomposite substrate may be redesigned and tested to find the optimal balance of mechanical performance and biodegradability. According to a preferred aspect of the present disclosure, a biodegradable sensor substrate is developed for the carrying, supporting or otherwise accepting circuitry (e.g., a PCB) for the duration in which environmental data will need to be collected, but then fully biodegrade into the soil (e.g., after one year) such as before the next growing season. By controlling the ratio of one constituent to another (e.g., biobased polymers and/or natural fibers), the biodegradation duration for a biocomposite substrate may be tailored to accommodate varying soil conditions, as mentioned above.

Direct Write Approach

Figure 2:
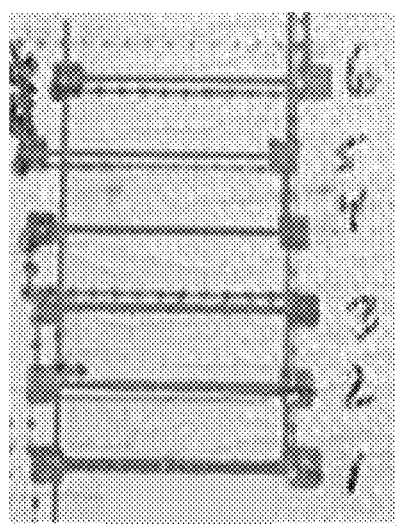
FIG. 2 is a pictorial representation of printed metallic traces on a biodegradable substrate in accordance with an illustrative embodiment.

According to an aspect of the disclosure, including at least one process, the coupons discussed above may be sectioned into squares and placed into the direct-write chamber of a direct-write system. Using the direct-write system, several 100 µm wide metallic lines (e.g., copper) were written on the square coupons and tested for conductivity, as shown in FIG. 2. This in accordance with a preferred aspect of this work exhibit the ability for metallic traces to be written onto a flexible, biobased substrate of the present disclosure without the use of high temperatures or caustic materials as are usually present/needed to create traditional printed circuit boards (PCBs).

Direct write processes, such as collimated aerosol beam direct write (CAB-DW), which uses liquid ink, and micro cold spray (MCS), which uses solid metallic particles may be used to print metallic traces onto a degradable substrate of the present disclosure. While CAB-DW can be used to create PCB interconnects, metallic inks tend to have lower conductivities (30-50% bulk) than MCS printed features which uses a metal aerosol and can have conductivities as high as 90% of bulk. Because MCS uses consolidated metal particles instead of liquid inks, there is no post-processing required, and the materials will not drip if printed on 3D surfaces. Therefore, a further aspect of the present disclosure is to create sensor interconnects and sensor antennas using MCS where both temperature sensitive and biodegradable structures on complex shapes may be needed.

Several materials for direct-writing various features of a sensor in accordance with the present disclosure are contemplated. For example, copper, while an excellent conductor, presents a problem because it can lead to soil toxicity. Aluminum and magnesium, however, provide one or more preferred alternatives. Aluminum is advantageous in that MCS may be used in air without the threat of oxidation while magnesium must be sprayed in an inert atmosphere glove box. Moreover, both aluminum and magnesium are naturally occurring through weathering of rocks and therefore pose little risk for soil and plant contamination, and neither material is strongly bioaccumulating. Both materials have bulk conductivities approximately half the magnitude of copper, and MCS may be configured to deliver bioinert printed traces with at least 50% bulk conductivity.

One approach uses MCS to write components of the sensor, such as for example, one or more interconnects, traces, and antennas. These components may be direct-written to a biodegradable substrate, using for example, the MCS direct-write system and methods for printed microelectronics disclosed in commonly owned International Publication WO 2013/158178 to NDSU Research Foundation, incorporated herein by reference in its entirety. The direct-write process may be used to write one or more components on a biodegradable substrate having a planar surface, or alternatively created on a planar surface that is then, for example, rolled into or direct-written on a 3D surface. Processes using 3D printing, such as stacked die, are contemplated herein for direct-writing one or more of the biodegradable components of the sensor onto a 3D surface. Beneficially, connections to an antenna and perhaps to the antenna itself may need to be printed on a curved surface, which is possible using MCS with, for example, a 5-axis motion system with a corresponding control system.

Sensors

According to another aspect of the present disclosure, sensor development contemplates various sensing modalities that allow for accurate determination of nutritive ions as well as pH and moisture levels within soil just to name a few. Each individual sensor may also be configured to measure temperature and one or more other quantities. Multiple sensors may be developed to accomplish one or more of the objectives of the present disclosure. The basis for sensor communications can be configured using, for example, an IDS SL13A high frequency (HF) integrated circuit (IC). This chip is commercially available. An example supplier of an HFIC chip type is AMS. The chip has basic RFID functionality as well as an internal temperature sensor and may also be connected to external capacitive, resistive or like sensors.

The present disclosure contemplates two primary avenues for ion detection. Both methods have been used for measuring soil properties, but in those applications, a soil sample is taken and ions are extracted by pumping water through the sample and over the sensor. Here, since the sensor is disposed in the ground, it would work fundamentally differently than the typical soil testing equipment. For example, the sensor could use ambient moisture, therefore requiring no pumping mechanism.

In one aspect, ion-sensitive field effect transistors (ISFET) may be used for ion detection. The ISFET uses a specialized insulating layer rather than $SiO_2$, such as silicon nitride, to generate a capacitive field in place of a metallic gate. The field will intensify with larger concentrations of the ion which comes into contact with the FET gate. One way to selectively monitor ion concentrations or pH is to place a semi-permeable, ion selective membrane over the gate.

According to another aspect, ion-selective microelectrodes may be used for sensing nutritive ions. This approach takes advantage of standard semi-conductor processes to create electrodes which are placed in contact with a semi-permeable membrane. The potential across the electrodes can be correlated to a concentration of the desired ion. Ion selectivity may be achieved using similar membranes to those used in ISFETS.

In keeping with one or more of the objectives of the present disclosure, exploration is undertaken to determine sensor integration parameters in keeping with the overall desired shape of the sensor, particularly when considering overall size. Power consumption and sensor drift are also contemplated in the selection process for one or more sensing mechanisms.

Another aspect contemplates placement of the sensing device within the sensor to maximize accuracy and minimize drift. The sensor is configured to operate in the presence of moisture and therefore finding a way for the sensor to operate in dry conditions and the sensing mechanism to be in contact with the moisture in the soil is preferred. To address these issues, aspects of the present disclosure include the use of a hydroscopic polymer layer made of hydroxyethyl cellulose, or similar material layers, beneath the ion-selective membrane. This layer encourages moisture diffusion and hence ion migration into the system where it can be measured while discouraging/controlling moisture ingress into other parts of the sensor.

Antenna

According to another aspect of the present disclosure, an antenna is configured so as to magnetically couple to a reader antenna, for example, at 13.5 MHz (HF). Using this type of operational mode is beneficial. First, moist soil can have a high dielectric, making electric coupling a poor choice. Second, in keeping with the size objectives of the sensor makes it more amenable to magnetic coupling. For example, an antenna operating at UHF frequencies falls outside the sensor size objectives of the present disclosure.

According to another aspect of the present disclosure, an HF antenna may be configured to use inductive coils. For example, the sensor may be configured on a substrate having a flat surface. If so, a planar coil can be created using a direct write process, such as the one disclosed in commonly owned International Publication WO 2013/158178. Direct-write printed materials include aluminum, magnesium and other bioinert materials contemplated herein. According to another aspect, the sensor may be configured to have a round or elliptical cross section. Taking this approach, a helical antenna could be printed (e.g., using a direct-write process) around the outer surface of the sensor or sensor substrate. This may be a preferable solution as the diameter of the coil would likely be larger than a planar coil, resulting in larger magnetic flux through the coil and hence better signal reception.

In another aspect, the present disclosure contemplates placement of the antenna on the sensor. Coils used for inductive coupling may have an omnidirectional radiation pattern. This is generally considered sufficient when reading randomly placed RFID as the probability that a sensor antenna and reader antenna would be completely orthogonal at all times (i.e., as the reader passes over the sensor) is assumed in most instances as unlikely. Further, if the sensors could be made inexpensively so that it was possible to place them with a relatively high density, missing one or two sensors may be of little consequence. Therefore, aspects of the present disclosure contemplate maximizing antenna effectiveness by controlled placement with a particular orientation in the sensor.

Encapsulation Approach

According to another aspect of the present disclosure, a biodegradable PCB is equipped with the appropriate circuitry and sensors, the entire system may be encapsulated in a biodegradable polymer which may be configured to provide a final shape of the sensor and protect the device during its transport and delivery into the soil (e.g., using standard agricultural seeding/planting equipment). Several processing methodologies are contemplated such as emulsion-solvent evaporation/extraction, phase separation-coacervation, interfacial deposition, and spray drying which can be used for encapsulation of the sensor, using biodegradable polymers. One contemplated encapsulation method includes meeting objectives of the present disclosure, such as, a) maintaining the performance of the circuitry and sensors through the curing process of the polymer, b) allowing consistent coverage and a repeatable final size, and c) allowing quick and even degradation of the encapsulating polymer shortly after introduction into the soil.

In one embodiment, a biodegradable encapsulation polymer comprising a polylactic-co-glycolic acid (PLGA) copolymer may be used. Other polymers are contemplated such as polyvinyl acetate (PVA) and like water soluble materials. The degradation rate of the encapsulation layer and its mechanical properties may be precisely controlled, for example, by varying the lactic acid/glycolic acid ratio through alternating the molecular weight of the polymers. PLGA polymers can be cleaved quickly into monomeric acids (i.e. lactic and glycolic acids) depending on the crystallinity, hydrophobicity, and molecular weight of the polymer in combination with the conditions of the environment it is being introduced into. Therefore, in accordance with one or more objectives of the present disclosure, an encapsulation polymer and its constituents may be selected, using for example ASTM Method D5988 to optimize the rate of biodegradation and therefore exposure of the sensors when introduced into the soil.

According to another aspect of the present disclosure, an encapsulation layer may be configured to support, enable or otherwise assist in one or more electrical functions of the sensor. For example, the degradable substrate could be configured to support electrical function. First, the encapsulation layer provides insulation from the surrounding soil. The ions and moisture in the soil, in effect, shield the antenna from an electrical signal or could potentially even short the antenna entirely. Creating an insulating layer between the antenna and soil helps minimize interference and maximize the ability for the sensor to communicate with a reader during its intended operational life. Second, an ion sensor as well as any other materials in the conductivity sensor and moisture sensor that are exposed to the soil degrade over time, resulting in a planned loss of accuracy and eventually function of the sensor. As a result, the various components (e.g., electronics) for ion sensing may potentially experience some drift that may be difficult to calibrate out. Thus, according to one aspect of the present disclosure, the biodegradable substrate is configured to degrade (e.g., the antenna and traces will crumble/collapse from lack of support) at the appropriate rate that the sensor will stop working before drift and degradation affect the accuracy of the sensor. In this manner, the amount of inaccurate data read from the sensor may be limited thereby limiting the potential for making inappropriate soil management decisions.

According to still another aspect, the encapsulation layer may include one or more nutrients, herbicides, pesticides or other like constituents that could be time-released into the surrounding soil as the encapsulation layer degrades over time thereby providing one or more benefits to the surrounding soil and plant life.

Objectives

In view of the forgoing, objects of the present disclosure include, amongst others, several of the following attributes. For example, sensor attributes of the one or more embodiments include:

1) Wireless operation, control and monitoring of the sensor;
2) Passive operation requires no battery or other connected power source (outlet);
3) RFID for communication with and powering a deployed sensor;
4) Subsurface sensor—entire sensor, including communications electronics, is buried or otherwise deployed beneath the soil surface, not just a sensor probe;
5) Sensor constructed with a biodegradable substrate;
6) Sensor uses non-bioaccumulating and non-toxic traces that decompose;
7) Sensor left in the soil to biodegrade;
8) Sensor may be configured with in-situ measurement of moisture using absorbent/resistive polymers (e.g., using diffusion to come to equilibrium with surrounding soil);
9) Sensor may be configured for in-situ measurement of nutrients/ions using, for example, ion-selective surfaces in relation to a reference probe (e.g., using diffusion to come to equilibrium with surrounding soil);
10) Sensor may be configured for in-situ measurement of pH using, for example, ion-selective surfaces in relation to a reference probe (e.g., using diffusion to come to equilibrium with surrounding soil);
11) Sensor may be configured for in-situ measurement of conductivity using, for example, one or more metal probes;
12) Sensor data may be collected in real-time using a reader;
13) Sensor may be deployed into soil using one or more automated deployment processes (e.g., seeder, planter or other like implement); and
14) Sensor may be configured commensurate with the size of a seed (e.g., soybean, corn, etc.) and on the order of less than 5 cm for its largest dimension.

Experimental

According to one experimental analysis, a biodegradable sensor, system and method are contemplated further herein. In one aspect, the approach includes the marriage of Radio Frequency Identification (RFID) technology with laminate layers of various polymer matrix composites, for example, RFID technology in polymer and polymer matrix composite structures. In accordance with one or more of the objectives of the present disclosure, composite materials are selected that are sufficiently transparent to radio waves. If radio waves cannot penetrate the material, the RFID tags will not function. Therefore, the signal strength through composites composed of different number of fiber layers are contemplated and tested to determine if radio waves could pass through, but also to what degree the signal strength was diminished.

Figure 3:
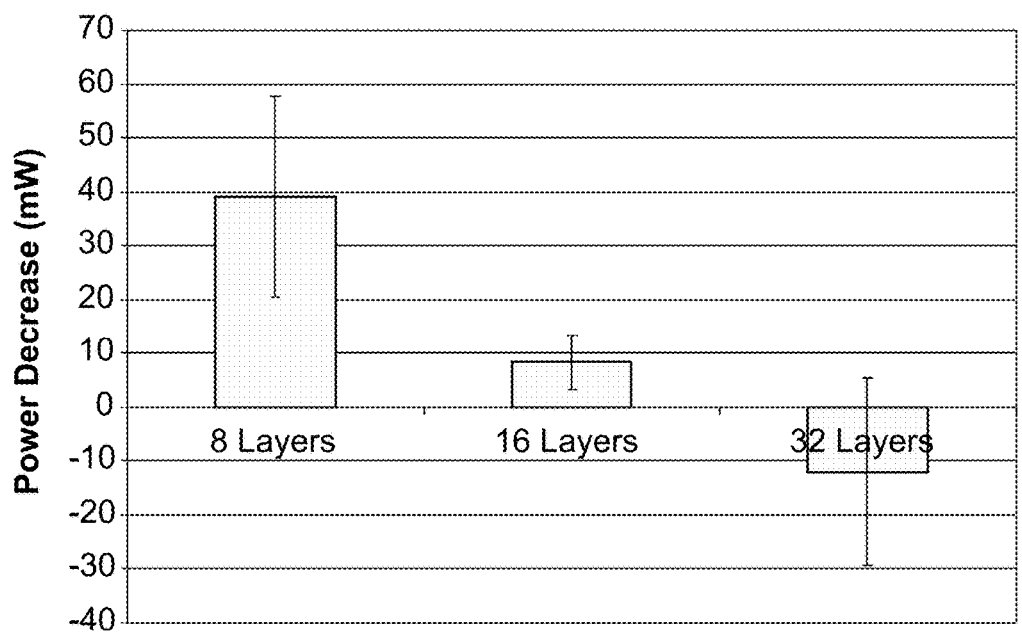
FIG. 3 is a pictorial representation of sensor activation power based on a material thickness in accordance with an illustrative embodiment.
Figure 4:
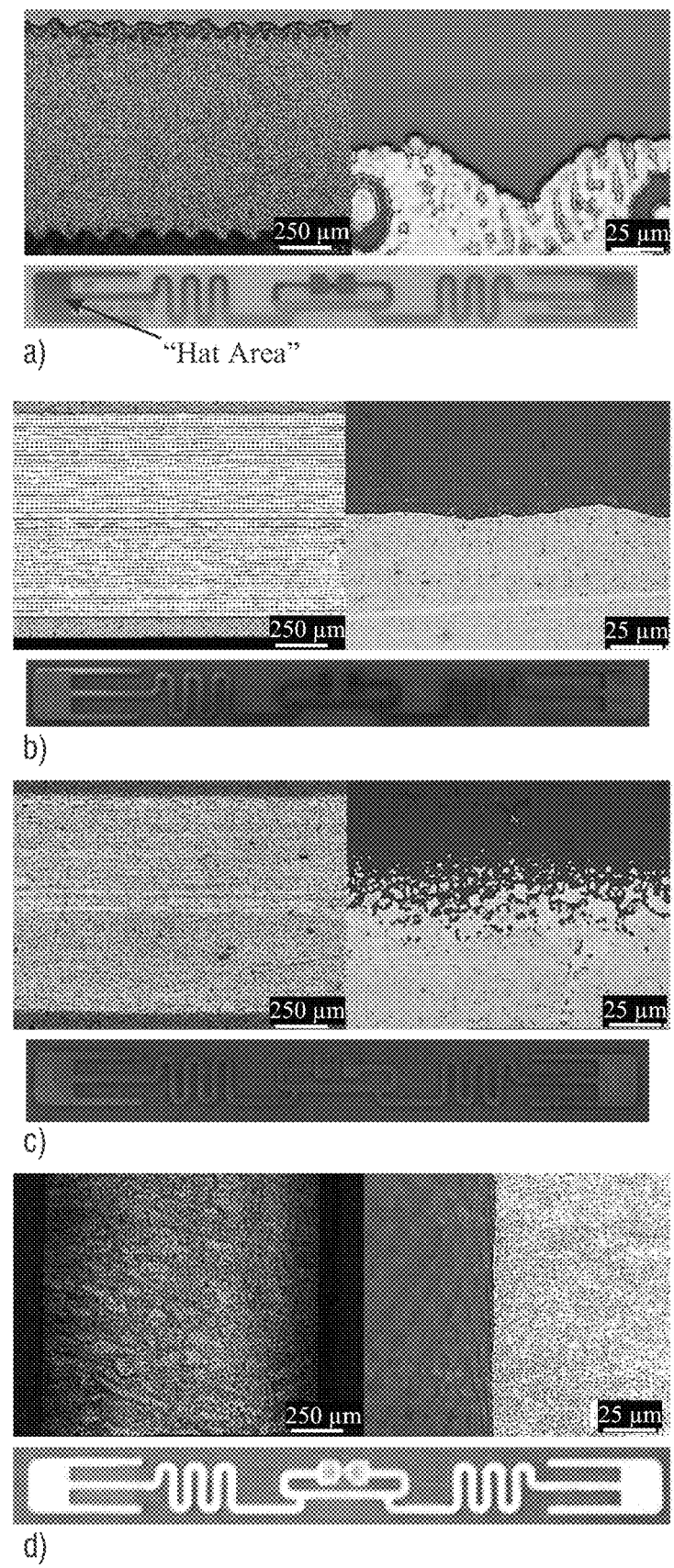
FIGS. 4(a)-4(d) are pictorial representations of antennas in accordance with an illustrative embodiment.

According to one test, tag signal strength was monitored. Specifically, RFID tags provided by Alien Technology were tested to determine the minimum activation power prior to any processing. The RFID tags were then embedded in composite panels of 8, 16 and 32 fiber layers and retested to see what effect the amount of fibers had. According to one test, panels were fabricated from Epoxy/E-glass and testing carried out at 910 MHz. As the amount of material through which the signal had to be sent increased, the strength of the signal decreased (see FIG. 3). The minimum power required to activate the RFID tags in the 8 and 16 E-glass layer panels actually decreased, meaning the signal strength increased. This may be attributed to the design of the RFID tags as they are intended to work over a range of frequencies, with the optimal frequency depending on the environment in which the tag is deployed. By changing the material surrounding the tag, the optimal operation frequency is moved closer to the testing frequency of 910 MHz. A noticeable and consistent difference in signal strength between the 8 and 16 layer panels is shown. For example, the panels composed of 32 layers tested showing a decrease in signal strength of about 12 mW. The results suggest that with an exponential increase in number of layers, the signal strength decreases linearly. Using this understanding, one or more designs for creating a biodegradable biocomposite PCB and a biodegradable polymer encapsulation approach in accordance with the objectives of the present disclosure are developed. Moreover, one or more components, structures or elements of the biodegradable sensor, such as the interconnects, traces, antenna, etc., may be direct-written using one or more non-heavy metals, bio-inert metals, such as aluminum and magnesium.

Direct-Write for RFID Tags

Aerosol Direct Write (A-DW) systems Aerosol Jet and CAB-DW along with MAPLE-DW shown and described in commonly owned International Publication WO 2013/158178 to NDSU Research Foundation are used to print silver nanoparticle based RFID antennas on Kapton® film. The antennas designed were based on "squiggle" patterns used by Alien Technology for their UHF 915 MHz band tags. Each antenna had different surface morphologies greatly depended on the type of A-DW tool used. FIGS. 4(a)-4(d) display each antenna, along with a detailed image of the surfaces, and edges where a) is the Copper etched antenna, b) is the CAB-DW printed antenna, c) is the Aerosol Jet printed Antenna, and d) is the MAPLE-DW printed antenna. After the printed traces were thermally post processed, RFID chips are attached, and the maximum read distance of the printed antenna RFID tags and commercially available copper-etched tags were measured. Even though the thicknesses of the direct-written antennas were much less than 1 μm, as compared to 4 μm for the copper etched tag, similar read distances were obtained. The results of this test are convincing evidence for the viability of using A-DW for the rapid prototyping of RFID antennas.

Figure 5:
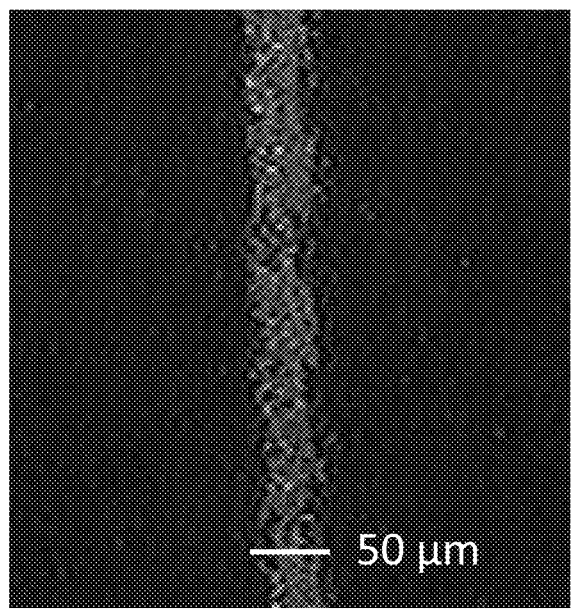
FIG. 5 is a pictorial representation of printed traces in accordance with an illustrative embodiment.

A Micro Cold Spray (MCS) system and process is shown and described in commonly owned International Publication WO 2013/158178 to NDSU Research Foundation. The approach involves shooting solid particles at a substrate at a velocity sufficient to cause them to deform and fuse together onto the substrate, allowing features to be created on a substrate without the high temperature required of most direct write and deposition systems. Embodiments of the present disclosure include the use of MCS as capable of printing traces from solid aerosols of tin, aluminum and copper onto various hard and flexible substrates. Formation of continuous lines depends upon both the substrate materials as well as the solid particles being deposited. Table 1 shows a list of exemplary substrates with a (+) or (−) designating whether or not a particular solid metal aerosol gave a continuous line. Electrical properties are measured for copper traces prepared using, for example, a 100 µm focusing nozzle, 400 ccm carrier gas (aerosol) flow, ~0.75 MPa accelerator (sheath) gas pressure, 0.5 mm stand-off distance and a 1 mm/s translation speed (greater speeds possible). The traces are ~50 µm wide (see FIG. 5) and have a resistivity of 1.9 µΩ-cm. In addition to metallic traces, the ability to fill vias from 75 µm to 150 µm in diameter with metals is demonstrated, providing an embodiment combining trace deposition and via filling into a single process.

TABLE 1

MCS material-substrate compatibility. Using this same process one or more bioinert materials may be direct-written onto the surface of a substrate.

| Substrate | Tin | Aluminum | Copper |
|---|---|---|---|
| Glass | + | + | + |
| Silicon | + | + | + |
| BT[1] | + | + | − |
| PEEK[2] | − | + | + |
| Kapton | + | + | − |
| Teflon | − | + | + |
| PES[3] | − | + | + |
| LCP[4] | − | + | + |
| Teslin | − | − | + |
| FR4[5] | − | + | − |
| Mylar | − | + | + |

Figure 7:
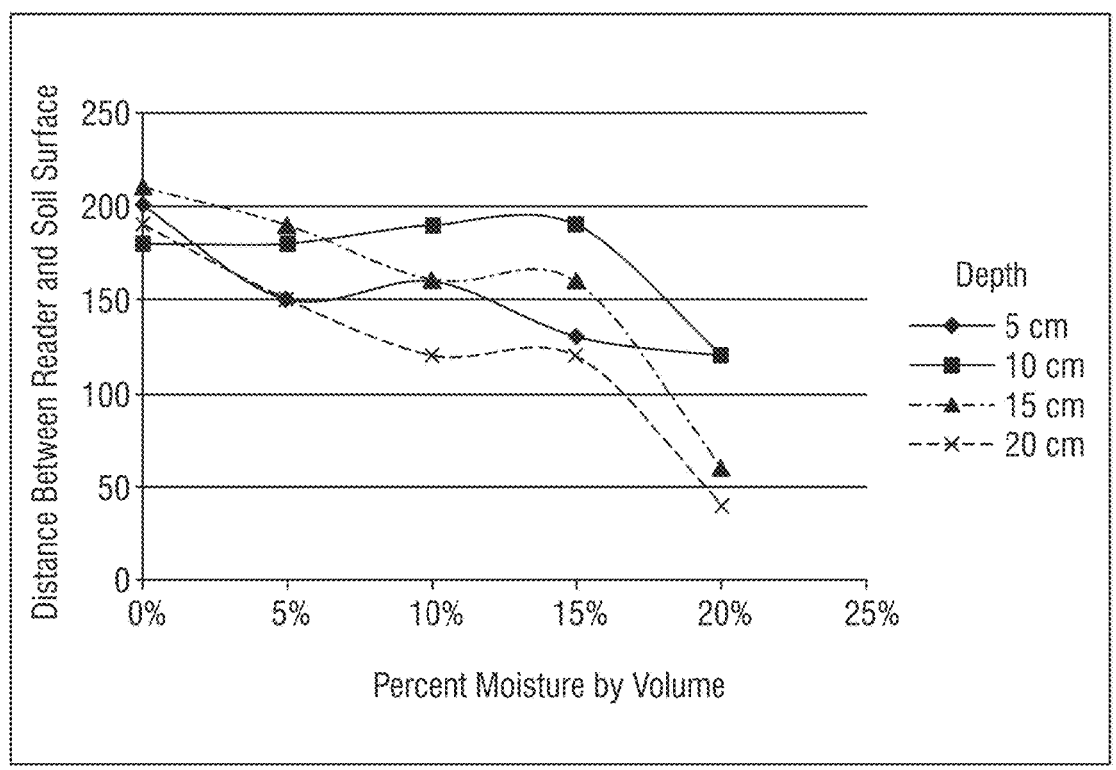
FIG. 7 is a pictorial representation of tags in varying soil depths and moisture levels in accordance with an illustrative embodiment.

[1]Fiberglass-reinforced Bismaleimide Triazine Epoxy
[2]Polyetherether ketone
[3]Polyethersulfone
[4]Liquid crystal polymer
[5]Glass-reinforced epoxy laminate Experiments to examine the communication capabilities of UHF RFID tags in varying soil depths and moisture levels are provided. For example, a UHF RFID transponder is placed up to 20 cm deep in up to 20% moisture by volume, the transponder is still able to communicate with a reader more than a meter away, in most cases. When moisture levels reached 20%, tags at 15 and 20 cm depths had to be read closer to a half meter. These results are shown in FIG. 7. An observation should be noted here, specifically that at 20% moisture levels, most farm implements would be unable to navigate in a field.

Antennas

According to at least one aspect of the disclosure, a novel passive UHF RFID tag that functions on metal is provided. The tag incorporates magnetic material and uses a metallic container as the antenna. This allows the sensor to be smaller than previously developed tags that are developed for on-metal use. According to one design, a field pattern that is omnidirectional with nulls in the plane of the antenna may be configured parallel to the feed structure between two slots. Because the gain pattern is omnidirectional, the sensor can be placed in virtually any orientation in the ground and should still be able to communicate. This may help prevent complete loss of communications if the soil becomes disturbed during the course of field testing. The antenna feed may be matched to the antenna input of the SL900A with a series capacitor in the 2-4 pF range. The antenna geometry may then be incorporated into a printed circuit board (PCB) layout of the present disclosure.

Sensors

Figure 6:
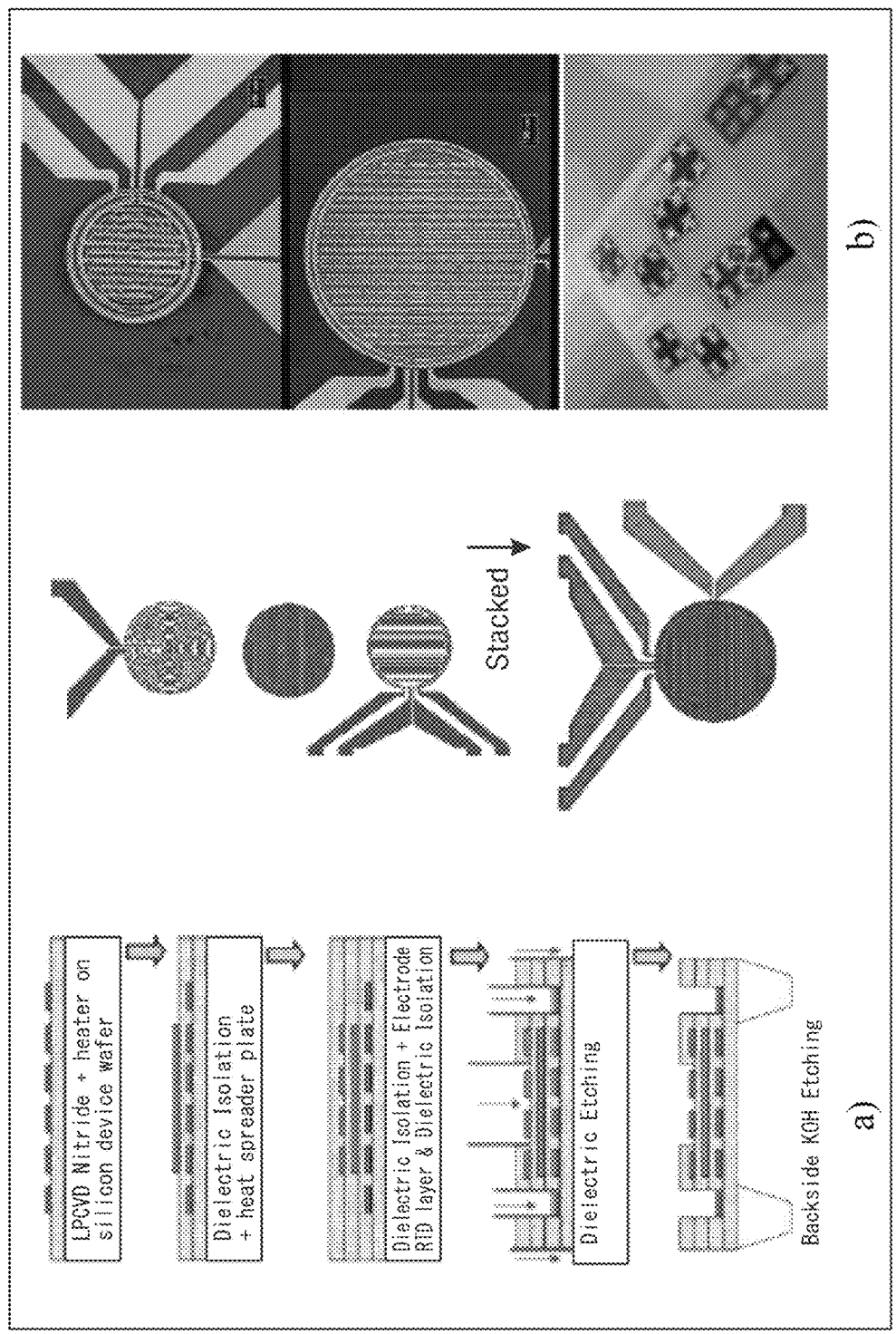
FIGS. 6(a)-6(b) are pictorial representations of a fabrication process in accordance with an illustrative embodiment.

Sensor elements may be configured to include a multi-layer design built up using traditional wafer fabrication processes in an in-house cleanroom. Several different sensing elements may be configured with active areas ranging from 130 µm to over 1 µm. The design consists of a patterned platinum micro-hotplate bottom layer on a nitride passivated silicon wafer, a second passivation layer, a platinum heat spreading layer, a third passivation layer, and finally a platinum interdigitated electrode with a surrounding resistance temperature detector (RTD). The contacts to the different layers may be opened using reactive ion etching (RIE). The fabrication process and an optical microscope image of a finished device are shown in FIG. 6(a)-6(b). A conductive polymer may be deposited on the surface of the interdigitated electrode, and as the polymer absorbed different chemical vapors, the resistance changes. Sensor elements of this type are successfully integrated into an embedded system which acted as an "electronic nose" which could detect ethanol vapors and provide a visual indication of an alarm, as well as store time-stamped data for review at a later date. Such sensor technology could be used to configure one or more designs of the present sensor to detect moisture in the sensor by loading the interdigitated electrode with a moisture absorbing polymer such as polyacrylic acid.

At least one sensing method for measuring soil conductivity (and therefore salinity and/or moisture content) may be based on the resistance between two probes of known geometry. For example, an AMS SL900A may be configured for use with one or more embodiments of the sensor. An AMS HFIC sensor as discussed herein includes, for example, constituents that biodegrade and are not bioaccumulating. The biodegradable constituents include 90% or more Silicon and small traces of gold and tin. There are several exemplary methods for connecting and measuring resistive sensors to the SL900A analog front end including using, for example, a wheatstone bridge, linear resistance using VSS as a reference, linear resistance using a rectified voltage from the RF field, resistive sensor with AC excitation, and resistive sensor with linear conductance. These connections may be tested using a variable resistor to determine the range of resistances that can be measured and their accuracy compared to a set value. The linear resistance with VSS reference allows for measuring resistances from 33.5 kΩ to more than 400 kΩ with an accuracy of 3-4%. The linear resistance with rectified RF voltage reference allows for measuring resistances from less than 100Ω to 79 kΩ with an accuracy of 2-3%. These two connection types provide an ability to accommodate a wide variety of electrode geometries and soil conductivities.

Figure 8:
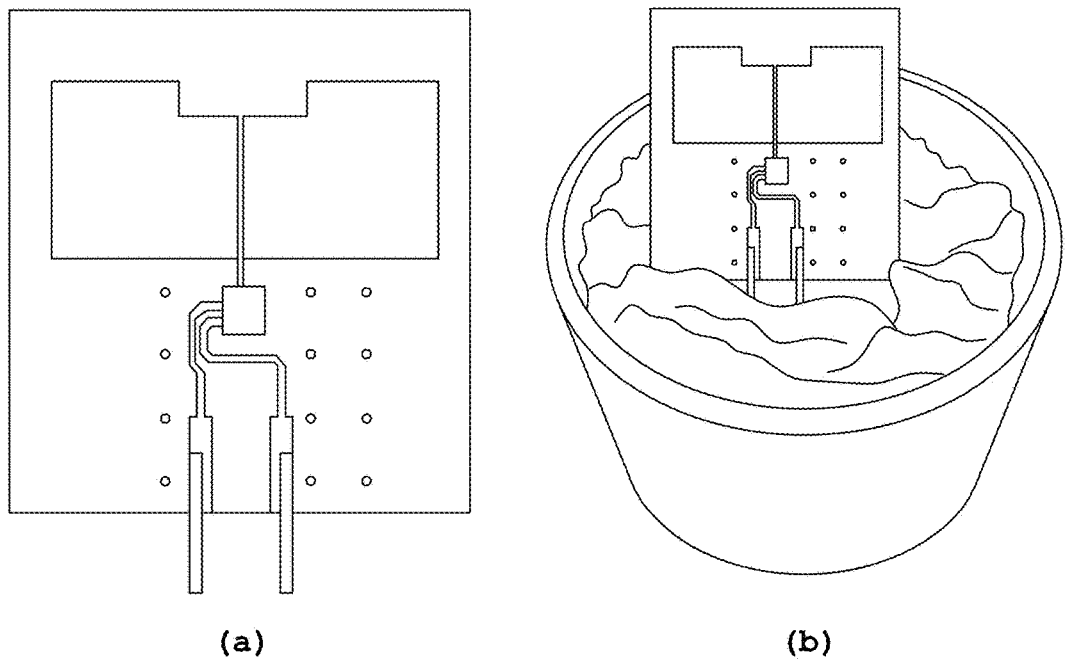
FIGS. 8(a)-8(b) are pictorial representations of a sensor for detecting moisture in accordance with an illustrative embodiment.

By way of example, a functional prototype is provided. The sensor includes, for example, a slot antenna built into the electronics ground plane and the AMS SL900A RFID IC along with two discrete capacitors. The sensor measures 57 mm×57 mm and is shown in FIGS. 8(a)-8(b). The prototype is configured to measure the resistance of soil which had measured amounts of water added to it. The resistance of the soil is used to calculate the resistivity, or inversely, the conductivity of the soil knowing the probe geometry. After the resistance measurement (through the RFID link), the mass of the soil and water is measured, and then the sample is baked overnight at 105° C. to evaporate the moisture in the soil. The mass of the dry soil may then be measured to determine the moisture content as tabulated in Table 2 below.

According to one embodiment, an SL900A includes an internal temperature sensor and incorporates UHF RFID communications in the 900-928 MHz ISM band with the option of including external sensor circuitry via a 10-bit A/D converter. The converter may be connected to conducting probes through a voltage divider. The probes, which have a well-defined geometry, may be configured to return a resistance measurement. The electronics components may be placed on a 57 mm×57 mm PCB containing a slot dipole. The antenna is preferably configured to harvest power from the reader and power the sensor passively. To communicate with the sensor, a reader development kit based on the R900G UHF RFID IC may be used. Software provided with the kit may allow for configuration of the SL900A and for reading the A/D values from the analog front end.

When the sensor is activated, the voltage increase across the probes generates a transient due to mobility of ions in the soil. This transient increases settling time. In order to minimize settling time, a voltage divider may be used. A reference voltage may be placed at one end of a known resistor while an excitation generates a voltage change across the probes. The reference voltage was set at 310 mV while the excitation voltage was 3 V. The voltage may be measured between the probes and known resistor. Modification of probe geometry as well as adjustment in reference voltage may allow for scaling of the range of resistance values to be measured. The resistance between the probes ($R_{SOIL}$) is given by $$R_{soil} = \frac{V_{exc} - V_{ref}}{V_{meas}} R_{ref} - R_{ref}$$

The resistivity to soil is given by $$\rho = \frac{R_{soil} A}{D}$$

where A is the area of metallization on the probe and D is the distance between probe tips. The conductivity of the soil ($\sigma$) is the reciprocal of the resistivity ($1/\rho$). Once the conductivity of the soil is known, empirical models can be used in conjunction with moisture levels and temperature to assess soil salinity.

The ability of the sensor to communicate and function in soil may be tested using a prototype without probes. For example, a square container holding dry soil may be placed at various distances from the reader antenna. For the purposes of testing, a coarse silty loam soil was chosen, which is an ideal agricultural soil. An Alien 9800 reader was attached to a bistatic antenna for the testing. The depth of the sensor was varied, and the maximum read distance was determined by moving the container away from the reader antenna until the sensor could no longer communicate with the reader.

The results indicate that the reader could consistently communicate with the sensor when it was within 0.8 m of the soil surface and the sensor was buried at depths up to 20 cm. It appears that the sensor communication performance increased at a depth of 10 cm and then decreased with increasing depth. This behavior is likely due to the dielectric behavior of the soil tuning and detuning the antenna as well as attenuation of the signal. Seed germination usually occurs at depths less than 10 cm. Corn, for example, is one of the deepest planted seeds at 6 cm. This depth for communication was therefore deemed acceptable performance. It is expected that the addition of moisture would increase the dielectric of the soil and decrease the maximum read range. The loss tangent would potentially also change if the additional moisture causes large scale ion migration. Increases in loss tangent would also negatively impact sensor communication range and decreases would result in increased read distance.

The resistance measurements were checked once it had been validated that the sensor would work when buried. A prototype was created with probes that were 5 mm long by 250 μm wide. The separation between the inner surface of the probes was 9.2 mm. A decade resistor box (iET RS-200 Resistance Substituter) was used to validate the performance of the analog front end. Eighteen different resistance levels between 630 kΩ and 3.4 MΩ were tested with a reference resistance of 62.9 kΩ in the voltage divider circuit. The resistance was first measured using a Fluke 189 True RMS Multimeter. The prototype conductivity sensor then measured the same resistance through leads attached between the probe tips and decade resistor box. The readings were generally very similar, and even at the largest resistances, the deviation between measurements was less than 7%.

TABLE 2

Soil moisture content measurements using RFID sensor.

| Sample Number | Measured Resistance | Resistivity ($\Omega$m) | Moisture Content ($\theta_g$, ratio of water to dry soil by mass) |
| --- | --- | --- | --- |
| 1 | 786 kΩ | 306.9 | 0.141 |
| 2 | 1.65 MΩ | 644.7 | 0.107 |
| 3 | 2.09 MΩ | 815.1 | 0.044 |

The present disclosure contemplates any number of sensor mechanisms (e.g., ion, conductivity, moisture, temperature, etc.) configured into the sensor. For example, an ion detection sensor could be configured into the sensor to measure ion levels in the surrounding soil. Ion sensors could be configured from one or more ion sensitive materials, polymers, transducing materials, or the like. In one aspect, an ion sensitive field-effect transistor (ISFET) may be configured to measure ion concentration. In another aspect, ion-selective microelectrodes may be used to measure ion concentration. For measuring temperature an HFIC, discussed above, may be used. The HFIC chip may also include one or more connects for external capacitive and resistive sensors contemplated herein. In any case, the sensors may be configured using one or more biodegradable materials allowing the sensor to be left in the soil after deployment thereby keeping with the objectives of the present disclosure.

The present disclosure is not to be limited to the particular embodiments described herein. In particular, the present disclosure contemplates numerous variations in the type of ways in which embodiments of the disclosure may be applied to a biodegradable soil sensor, a biodegradable soil sensing system and method for obtaining soil information. The foregoing description has been presented for purposes of illustration and description. It is not intended to be an exhaustive list or limit any of the disclosure to the precise forms disclosed. It is contemplated that other alternatives or exemplary aspects that are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the disclosure disclosed with greater particularity.

REFERENCES

1. F. Baret and S. Buis, "Estimating canopy characteristics from remote sensing observations: review of methods and associated problems," *Advances in Land Remote Sensing*. New York, USA. Springer, pp. 173-201, 2008.
2. H.-J. Kim, K. A. Sudduth, and J. W. Hummel, "Soil macronutrient sensing for precision agriculture," *Journal of Environmental Monitoring*, vol. 11, pp. 1810-1824, 2009.
3. K. D. Shepherd and M. G. Walsh, "Infrared spectroscopy—enabling an evidence-based diagnostic surveillance approach to agricultural and environmental management in developing countries," *Journal of near Infrared Spectroscopy*, vol. 15, pp. 1-19, 2007.
4. R. Kumar, M. K. Yakubu, and R. D. Anandjiwala, "Biodegradation of flax fiber reinforced poly lactic acid," *Express Polymer Letters*, vol. 4, pp. 423-430, July 2010.
5. J. K. Oh, "Polylactide (PLA)-based amphiphilic block copolymers: synthesis, self-assembly, and biomedical applications," *Soft Matter*, vol. 7, pp. 5096-5108, 2011.
6. S. Pilla, *Handbook of Bioplastics and Biocomposites Engineering Applications* vol. 81: Wiley-Scrivener, 2011. Available: http://www.natureworksllc.com
7. R. L. Shogren, W. M. Doane, D. Garlotta, J. W. Lawton, and J. L. Willett, "Biodegradation of starch/polylactic acid/poly(hydroxyester-ether) composite bars in soil," *Polymer Degradation and Stability*, vol. 79, pp. 405-411, March 2003.
8. Y. Tokiwa, B. P. Calabia, C. U. Ugwu, and S. Aiba, "Biodegradability of Plastics," *International Journal of Molecular Sciences*, vol. 10, pp. 3722-3742, September 2009.
9. J. H. Park, M. L. Ye, and K. Park, "Biodegradable polymers for microencapsulation of drugs," *Molecules*, vol. 10, pp. 146-161, January 2005.
10. L. Maderova, M. Watson, and G. I. Paton, "Bioavailability and toxicity of copper in soils: Integrating chemical approaches with responses of microbial biosensors," *Soil Biology and Biochemistry*, vol. 43, pp. 1162-1168, 2011.
11. S. Bhattacharya, A. Lutfurakhmanov, J. M. Hoey, O. F. Swenson, and R. A. Sailer, "Micro Cold Spray Direct Write Process," presented at the ASME International Mechanical Engineering Congress and Exposition, Houston, Tex., USA, 2012.
12. *SL13A Single-Chip Data Logger with Sensor*. Available: http://www.ids-microchip.com/upload/3550902-SL13-PF.pdf
13. S. J. Birrell and J. W. Hummel, "Real-time multi ISFET/FIA soil analysis system with automatic sample extraction," *Computers and Electronics in Agriculture*, vol. 32, pp. 45-67, 2001.
14. K. Tsukada, M. Sebata, Y. Miyahara, and H. Miyagi, "Long-life multiple-ISFETS with polymeric gates," *Sensors and Actuators*, vol. 18, pp. 329-336, 1989.
15. P. Bergveld, "ISFET, theory and practice," in *IEEE Sensor Conference Toronto*, 2003, p. 1.
16. O. T. Guenat, S. Generelli, N. F. de Rooij, M. Koudelka-Hep, F. Berthiaume, and M. L. Yarmush, "Development of an Array of Ion-Selective Microelectrodes Aimed for the Monitoring of Extracellular Ionic Activities," *Analytical Chemistry*, vol. 78, pp. 7453-7460, 2006 Nov. 1, 2006.
17. A. Uhlig, E. Lindner, C. Teutloff, U. Schnakenberg, and R. Hintsche, "Miniaturized Ion-Selective Chip Electrode for Sensor Application," *Analytical Chemistry*, vol. 69, pp. 4032-4038, 1997 Oct. 1, 1997.
18. A. Ul Hague, M. Rokkam, A. De Carlo, S. Wereley, H. Wells, W. McLamb, S. Roux, P. Irazoqui, and D. Porterfield, "Design, Fabrication and Characterization of an In Silico Cell Physiology lab for Bio Sensing Applications," in *Journal of Physics: Conference Series*, 2006, p. 740.
19. K. Finkenzeller, *RFID handbook: fundamentals and applications in contactless smart cards, radio frequency identification and near-field communication*: Wiley, 2010.
20. J. M. Hoey, M. T. Reich, A. Halvorsen, D. Vaselaar, K. Braaten, M. Maassel, I. S. Akhatov, O. Ghandour, P. Drzaic, and D. L. Schulz, "Rapid prototyping RFID antennas using direct-write," *IEEE Transactions on Advanced Packaging*, vol. 32, pp. 809-815, November 2009.
21. J. M. Hoey, A. Lutfurakhmanov, D. L. Schulz, and I. S. Akhatov, "A review on aerosol-based direct-write and its applications for microelectronics"*Journal of Nanotechnology*, vol. 2012, pp. 1-22, 2012.
22. C. Bauer-Reich, L. Berge, and M. Reich, "Low-profile, high-permeability antennaless RFID tags for use on metal objects," in *Antenna Technology (iWAT), 2012 IEEE International Workshop on*, 2012, pp. 32-35. 1997.

What is claimed is:

1. A soil sensor comprising:
    one or more electrically conductive bioinert traces;
    a biodegradable substrate having a printed circuit of the one or more electrically conductive bioinert traces, said biodegradable substrate comprising a renewable resource in combination with a reinforcement of natural fibers;
    an antenna formed by at least one of the one or more electrically conductive bioinert traces;
    a sensor connected to at least one of the one or more electrically conductive bioinert traces, wherein said sensor is passive and does not require a battery or power source; and
    a biodegradable encapsulation layer housing the biodegradable substrate and the electrically conductive bioinert traces.

2. The soil sensor of claim 1 wherein the one or more electrically conductive bioinert traces comprise one or more biodegradable bioinert metals.

3. The soil sensor of claim 1 wherein the one or more electrically conductive bioinert traces comprise one of:
    a. aluminum;
    b. magnesium.

4. The soil sensor of claim 1 wherein the biodegradable substrate comprises a biodegradable biocomposite substrate.

5. The soil sensor of claim 1 wherein at least one sensor uses ion-sensitive field effect transistors or ion selective microelectrodes.

6. The soil sensor of claim 1 wherein the biodegradable substrate comprises one or more biodegradable polymers.

7. A method for obtaining soil information comprising:
providing a biodegradable encapsulated sensor having one or more electrically conductive bioinert traces carried by a biodegradable substrate comprising a renewable resource in combination with a reinforcement of natural fibers, wherein the biodegradable sensor is passive and does not require a battery or power source;
depositing the biodegradable encapsulated sensor underground;
sensing one or more soil-related parameters with at least one of the one or more electrically conductive bioinert traces;
collecting the one or more soil-related parameters with a reading device emitting radio frequencies that power the sensor and receive information therefrom; and
leaving the biodegradable sensor in the soil to biodegrade.

8. The method of claim 7 further comprising:
depositing the biodegradable encapsulated sensor underground using one of:
a. a seed planter;
b. a seeder;
c. a field implement.

9. The method of claim 7 further comprising:
encapsulating the biodegradable sensor in a biodegradable polymer.

10. The method of claim 7 further comprising:
tailoring one or more properties for the biodegradable encapsulated sensor for controlling degradation rates of the biodegradable substrate and the one or more electrically conductive bioinert traces.

11. The method of claim 7 further comprising:
adding one or more natural fibers to the biodegradable substrate for tailoring a rate of degradation for the biodegradable substrate.

12. The method of claim 7 further comprising:
forming an encapsulating layer around the one or more electrically conductive bioinert traces and substrate commensurate in size and shape of a seed.

13. The method of claim 7 further comprising:
measuring the one or more soil-related parameters with an absorbent/resistive polymer.

14. A soil sensing system comprising:
a biodegradable soil sensor having one or more biodegradable components comprising:
a. a substrate comprising a renewable resource in combination with a reinforcement of natural fibers;
b. a plurality of printed electrical traces;
c. a circuit with one or more of the plurality of printed electrical traces;
d. at least one sensing element connected to one or more of the plurality of printed electrical traces;
e. an antenna formed by at least one or more of the plurality of printed electrical traces;
a reading device for collecting one or more soil-related parameters from the biodegradable soil sensor, said reading device emitting a radio frequency to both power the sensor and to receive information from said sensor;
wherein the biodegradable soil sensor is passive and does not require a battery or power source.

15. The soil sensing system of claim 14 wherein the substrate comprises a biodegradable composite comprising a natural polymer and at least one natural fiber.

16. The soil sensing system of claim 14 wherein the plurality of printed electrical traces comprise one or more non-heavy metals printed by a micro cold spray direct-write process.

17. The soil sensing system of claim 14 wherein the at least one sensing element comprises one of:
a. an ion sensor;
b. a conductivity sensor;
c. a moisture sensor;
d. a temperature sensor.

18. The soil sensing system of claim 14 wherein the circuit comprises a high frequency integrated circuit.

19. The soil sensing system of claim 14 further comprising an encapsulation layer having one or more natural fibers.

20. The soil sensing system of claim 14 wherein the sensing element comprises a biodegradable ion-selective polymer.

21. The soil sensing system of claim 14 wherein the reading device is attached to an implement for powering the circuit.

* * * * *